United States Patent [19]
Gordon

[11] Patent Number: 5,324,413
[45] Date of Patent: Jun. 28, 1994

[54] ELECTROPHORESIS CAPILLARY WITH DISPERSION-INHIBITING CROSS-SECTION

[75] Inventor: Gary B. Gordon, Saratoga, Calif.

[73] Assignee: Hewlett-Packard Company, Palo Alto, Calif.

[21] Appl. No.: 938,665

[22] Filed: Aug. 31, 1992

Related U.S. Application Data

[63] Continuation of Ser. No. 402,931, Sep. 5, 1989, abandoned, which is a continuation-in-part of Ser. No. 319,460, Mar. 6, 1989, Pat. No. 5,061,361.

[51] Int. Cl.$^5$ .................... G01N 27/26; G01N 27/447
[52] U.S. Cl. .............................. 204/299 R; 204/180.1
[58] Field of Search .............. 204/299 R, 180.1, 183.3

[56] References Cited

U.S. PATENT DOCUMENTS

| | | | |
|---|---|---|---|
| 4,578,167 | 3/1986 | Schoner | 435/287 X |
| 4,690,749 | 9/1987 | Van Alstine et al. | 204/299 R |
| 4,902,629 | 2/1990 | Meseral et al. | 436/165 |
| 5,092,973 | 3/1992 | Zare et al. | 204/299 R X |

OTHER PUBLICATIONS

P. Bocek, M. Deml, & J. Janák "Instrumentation for High Speed Isotachophorcsis" Journal of Chromatography, 106 (1975) 283-290.
M. Janssom, A. Emmer, & J. Roeraade "Some Design Considerations in Miniaturized Electrokimetic Separation Systems" Journal of High Resolution Chromatography 12 (1989) 797-801.
J. F. Brown and J. O. N. Hinckley "Electrophoretic Thermal Theory III, Steady-State Temperature Gradients in Rectangular Section Columns" Journal of Chromatogrpahy 109 (1975) 225-231.
M. Coxon and M. J. Binder "Transverse Temperature Distributions in Isotachophoresis Columns of Rectangular Cross-Section" Journal of Chromatography, 107 (1975) 43-50.
P. Bocek, Z. Ryslavy, M. Deml, & J. Janák "Stationary Mean Temperatures and Radial Temperature Profiles in Capillary Isotachophoresis" Collection Czechoslov. Chem. Commun. 42 (1977) 3382-3387.
Z. Ryslavy, P. Bocek, M. Deml & J. Janák "Effects of Joule Heat on the Steady-State Temperature Profiles and the Means Values of Temperature in Isotachophoresis" Journal of Chromatography 144 (1977) 17-25.
Arne Tiselius, "A New Apparatus for Electrophoretic Analysis of Collodal Mixtures" Transactions of the Faraday Society 33 (1937) 524-530.

(List continued on next page.)

Primary Examiner—John Niebling
Assistant Examiner—John S. Starsiak, Jr.

[57] ABSTRACT

An Electrophoresis Capillary with Dispersion-Inhibiting Cross-Section for providing unprecedented levels of detection sensitivity of solutes in a separation column is disclosed. The higher level of sensitivity is accomplished by utilizing larger sample volumes contained in capillaries having non-circular cross-sections. The present invention avoids the unwanted turbulence, viscosity gradients, and gravity siphoning that plague previous conventional devices that employ circular capillaries having equivalent cross-sectional areas. The key to the enhanced performance that is achieved using the present invention is a novel non-circular capillary which has a cross-sectional configuration that maximizes the central area of the capillary without creating the conditions that cause uneven flow through the capillary. The capillary portrayed in FIG. 3(a) has a generally oblong cross-section. An exterior surface encloses a capillary wall which defines two generally radial channels that extend in opposite directions from the center of the capillary along its transverse axis. The maximum width of each channel is approximately fifty microns. The ratio of the length and width of the channels is generally equal to two or greater. Alternative embodiments include circular capillaries that enclose solid filaments. The invention is also designed for use with an integrally-formed, expanded detection cell. The present invention combines the selectivity of a conventional, smaller, round capillary with the sensitivity of a capillary which is ten times larger.

1 Claim, 7 Drawing Sheets

OTHER PUBLICATIONS

James W. Jorgenson "Chapter 13-Capillary Zone Electrophoresis" New Directions in Electrophoretic Methods, edited by Jorgenson & Phillips (1987) 182-198.

M. Jansson, A. Emmer, & J. Roeraade "Some Design Considerations in Miniaturized Electrokinetic Separation Systems" Journal of High Resolution Chromatography vol. 12 (Dec. 1989) pp. 797-801.

M. Coxon and M. J. Bocek, M. Deml, & J. Janak "Effects of Joule Heat on the Steady-State Temperature Profiles and the Mean Values of Temperature in Isotachophoresis" Journal of Chromatography, 144 (1977) pp. 12-25.

Arne Tiselius, "A New Apparatus for Electrophoretic Analysis of Colloidal Mixtures" Transactions of the Faraday Society 33 (1937) pp. 524-530.

P. Gabauer et al., Determination of nitrate, chloride and suplhate in drinking water by capillary freezone electrophoresis, 1983, Elsevier Science Publishers B.V., pp. 455-457.

Karin D. Caldwell, Field Flow Fractionation, Sep. 1, 1988, vol. 60, No. 17, Analytical Chemistry, pp. 959-971.

Manuel J. Gordon, et al., Capillary Electorphoresis, Oct. 14, 1988, Science, vol. 242, pp. 224-228.

Xiaohua Huang, et al., Quantitative Analysis of Low Molecular Weight Carboxylic Acids by Capillary Zone Electrophoresis/Conductivity Detection, Apr. 1, 1989, Analytical Chemistry, vol. 61, No. 7, pp. 766-770.

ELECTROPHORESIS CAPILLARY WITH DISPERSION-INHIBITING CROSS-SECTION

CROSS-REFERENCE TO A RELATED PATENT APPLICATION

This is a continuation of copending application Ser. No. 402,931 filed on Sep. 5, 1989, now abandoned, which is a continuation-in-part of the Applicant's commonly-assigned, pending U.S. application Ser. No. 319,460 now U.S. Pat. No. 5,061,361 on Mar. 6, 1989 and which is entitled "Capillary Zone Electrophoresis Cell System". The prior application is hereby incorporated by reference.

BACKGROUND OF THE INVENTION

The present invention is an apparatus for separating unknown solutes in a buffer solution. This invention is particularly concerned with the recognition of large biological materials which are transported through a fine capillary using chemical electrophoresis techniques.

Recent advances in biotechnology have accelerated the demand of research laboratories, health-care facilities, and pharmaceutical manufacturers for devices which are capable of accurately and rapidly identifying extremely small quantities of inorganic and organic substances. Previous techniques, which include gas and liquid chromatography, have been employed to assay samples whose molecular structure is relatively small. Although chromatography may be successfully employed to resolve mixtures of inorganic and small organic molecules; the very large and exceedingly complex molecules of amino acids, proteins, peptides, and DNA are more difficult to separate than the smaller molecules. Another serious flaw in chromatographic methods is the predicament that is encountered when the unknown sample is especially sparse, since chromatography utilizes relatively large amounts of the material which requires analysis. Other shortcomings that are experienced when liquid chromatography is practiced include inconsistent patterns of solute movement through the system which creates uneven flows called "dead zones" and undesirable laminar mixing as opposed to plug movement of the fluids.

Electrophoresis is another well-known procedure that enables the researcher or scientist to evaluate undetermined materials. Capillary electrophoresis utilizes an electric field which is imposed across a length of tubing or capillary that contains a mixture of the unknown sample and a non-reactive liquid often called a buffer solution. The electric field creates an electro-osmotic flow and causes the buffer and the constituents of the unknown sample to be pulled through the capillary. The electric field also creates a superimposed electrophoretic flow which separates the constituents of the sample according to their varying molecular drags and varying net electrical charges. Because dissimilar substances do not react to the drag and electrical attraction in the same way, they become increasingly separated into distinct zones or groups as they progress along the capillary. Each band of constituent material that makes up the original unseparated mixture of unknown material passes through the capillary by itself. At some point along this tubing, each band is examined and identified by a detector. One type of detector for electrophoretic separations measures the electrical conductivity of the bands in the capillary. An alternative detection scheme is a method called laser induced fluorescence. Although this technique is highly sensitive, it is costly and is limited to detecting compounds that fluoresce or which can be stimulated to do so.

Another previous system probes the unknown material by shining ultra-violet light through an unknown solute borne by a buffer solution and then gauging how much light is absorbed by the solute. This radiation absorption method is the most popular technique among the various available electrophoretic systems. The capillaries in this system must be kept very narrow so that all the material inside it moves without turbulence or eddy currents. This uneven flow is created when the electrical current that passes through the contents of the capillary heats the buffer solution. This heat is conducted radially from the center of the tube out to its periphery. The migration of heat establishes a radial thermal gradient, extending from a relatively hot zone at the center of the capillary to cooler temperatures at the capillary wall. These different heat levels across the vessel set up convection currents within the buffer solution that tend to mix the contents of the capillary in directions that are perpendicular to the flow of liquid and solute through the capillary tube. This mixing destroys the sensitivity of the electrophoretic separation instrument because it tends to broaden the bands of separated solute. Another problem caused by this uneven heating in the capillary is the creation of viscosity gradients that also tend to broaden the solute bands. Most separation systems are also beset by an undesirable condition called gravity siphoning. When the two ends of the separation capillary are not precisely aligned, the difference in their heights causes an unwanted flow due to the efforts of gravitational forces to equalize the height of the contents of each column.

Conventional systems have been designed to minimize unwanted turbulence, viscosity gradients, and gravity siphoning by utilizing capillaries that are extremely narrow. Capillaries having relatively small cross-sections reduce uneven heating which generates unwanted eddy currents and viscosity gradients. The detriment suffered by this compromise is the severe reduction in sample size that can be analyzed by the detector at any given time. This relatively small sample volume which may be processed at any one time is a serious difficulty that is shared by all previous detection methods. To prevent undesirable dispersion of the solute caused by large thermal gradients, the diameter of conventional circular capillaries is usually kept at or below one hundred microns. Fifty microns is a common size for these capillaries. As a consequence, the sensitivity of conventional systems is limited to a level far below the one-part-per-million threshold, which is the current desirable detection accuracy which should be achieved to analyze mixtures of inorganic and small organic molecules.

As the technology of genetic engineering continues to evolve, diagnostic and measurement techniques which are more accurate, reliable, and sensitive become increasingly more valuable. Doctors, clinicians, and laboratory technicians need more powerful tools to explore the intricacies of the genetic code, to improve the hardiness and usefulness of plant and animal life in an effort to feed the world's burgeoning population, and ultimately to devise cures for inherited disabilities and dreaded diseases. The problem of providing a highly sensitive and precise separation system that overcomes the limitations that impair previous devices and techniques has presented a challenge to designers and innovators in the biochemical arts. The development of an effective and sensitive system for separating the components of an unknown biological sample would constitute a major technological advance in the biochemical and biotechnology industries. The enhanced performance that could be achieved using such an innovative device would satisfy a long felt need within the business and would enable manufacturers of drugs, medicines, and biological products to save substantial expenditures of time and money.

SUMMARY OF THE INVENTION

The Electrophoresis Capillary with Dispersion-Inhibiting Cross-Section disclosed and claimed in this patent application provides a higher level of detection sensitivity for any given detector technique than previous electrophoretic separation equipment. The higher level of sensitivity is accomplished by utilizing larger sample volumes contained in capillaries having non-circular cross-sections. The present invention avoids the unwanted turbulence that plagues previous conventional devices that employ circular capillaries having equivalent cross-sectional areas. The key to the enhanced performance that is achieved using the present invention is a novel non-circular capillary which has a cross-sectional configuration that maximizes the central area of the capillary without creating the conditions that cause uneven flow through the capillary. This capillary may be used to great advantage in combination with the inventor's previous invention, the Capillary Zone Electrophoresis Cell System.

The present invention utilizes a narrow bore capillary having one or more channels whose maximum width is approximately fifty microns. The preferred embodiment is a generally oblong capillary that resembles a rectangle with rounded ends which provides a much larger cross-sectional area for the transportation of solute in a buffer solution, while maintaining the optimal width that limits solute mixing. Alternative embodiments include configurations that resemble lens-shaped or lenticular cross-sections, rectangular and elliptical profiles, open figure-eights, and asterisk patterns. Another set of alternative forms of the invention include outer capillaries that enclose solid filaments having various shapes.

The Electrophoresis Capillary with Dispersion-Inhibiting Cross-Section is a novel device that offers unprecedented sensitivity in the electrophoretic detection of unknown solutes. The apparatus claimed in this patent application provides an effective, efficient, and powerful tool that will enable engineers and scientists in the medical instrumentation industry to construct valuable analysis equipment that will contribute to the advancement of the field of biotechnology.

An appreciation of other aims and objectives of the present invention and a more complete and comprehensive understanding of this invention may be achieved by studying the following description of a preferred embodiment and by referring to the accompanying drawings.

BRIEF DESCRIPTION OF THE DRAWINGS

FIGS. 1 through 9 are each cross-sectional views.

FIGS. 4(a) through 9 display alternative embodiments of the Applicant's invention. The capillary in FIG. 4(a) has an oval configuration, while that in FIG. 4(b) resembles a figure-eight.

FIGS. 6, 7, and 8 illustrate a circular capillaries which each enclose a solid circular filament. The filament in FIG. 7 has three contact appendages.

DETAILED DESCRIPTION OF A PREFERRED EMBODIMENT

Figure 1:
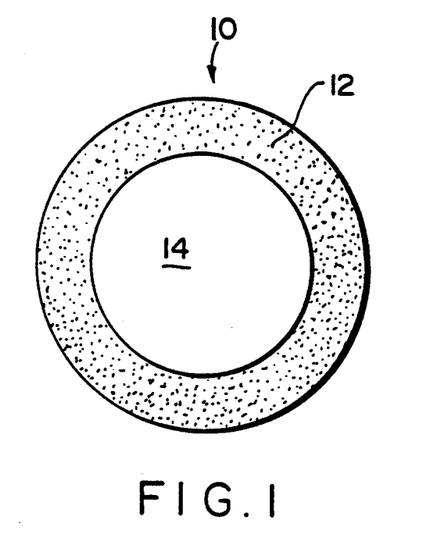
FIG. 1 depicts a conventional circular capillary having a large inside diameter of one hundred and fifty microns.
Figure 2A:
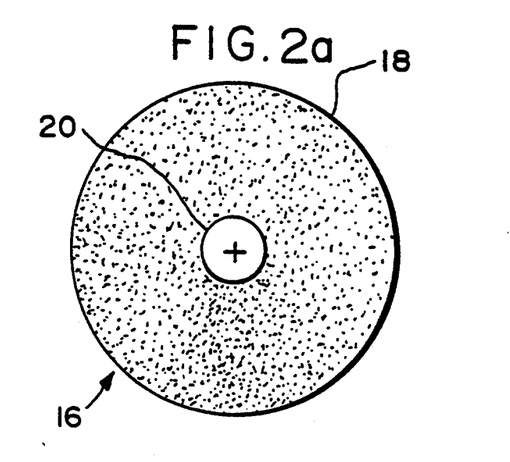
FIG. 2(a) reveals a conventional narrow-bore circular capillary having an inside diameter of fifty microns.
Figure 2B:
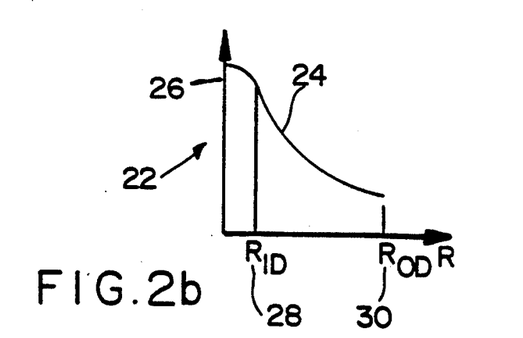
FIG. 2(b) illustrates the relationship between the temperature of the contents of the capillary and a given radius for the capillary shown in FIG. 2(a).

FIG. 1 depicts an artificially large conventional capillary with an exaggerated circular cross-section 10. The distance between the capillary wall 12 and the center of the central area 14 is relatively large compared to the capillary 16 shown in FIG. 2(a). Capillary 16 has an outside diameter 18, but its inside diameter 20 is far less than that of capillary 10. When capillary 10 is used in an electrophoresis separation device, turbulence and undesirable mixing is caused by the radial thermal gradient that is created when the buffer solution carried by the capillary is heated by the electrical field imposed across the capillary that drives the separation process. The deleterious turbulence and eddy currents ruin the ability of capillary to separate the mixture of unknown compounds into distinct bands. This unwanted mixing can be substantially reduced by using a narrow bore capillary like the one illustrated in FIG. 2(a). The thermal gradient generated by the smaller central area keeps the turbulence at tolerable levels. FIG. 2(b) presents a graph 22 of temperature vs. radial position within the capillary 16. Curve 24 indicates that the highest temperature 26 within the capillary 16 may be found at its center. The temperature at the inside diameter 28, labeled Ria, is somewhat lower than the center; while the heat level at the outside diameter 30, labeled Roa, is the lowest point on the temperature curve.

The compromise of trading sample volume for reduced turbulence, however, has a severe consequence: the volume of unknown sample that can be detected at any given time, and therefore, the sensitivity of the electrophoretic separation instrument, are both greatly diminished. The Electrophoresis Capillary with Dispersion-Inhibiting Cross-Section 32 revealed in FIG. 3(a) eliminates this inexpedient compromise by increasing the sensitivity of the detector without tolerating the harmful convection mixing, viscosity gradients, and gravity siphoning. The preferred embodiment of the present invention employs a capillary having a generally non-circular cross-section. The innovative design approach shared by all the embodiments of the present invention is the simultaneous use of the largest possible cross-sectional capillary area and the shortest width of the channels which convey the solute and buffer solution through the capillary. The sample capacity of the capillary is an order of magnitude greater than that of a conventional round capillary having an equivalent channel width.

Figure 3A:
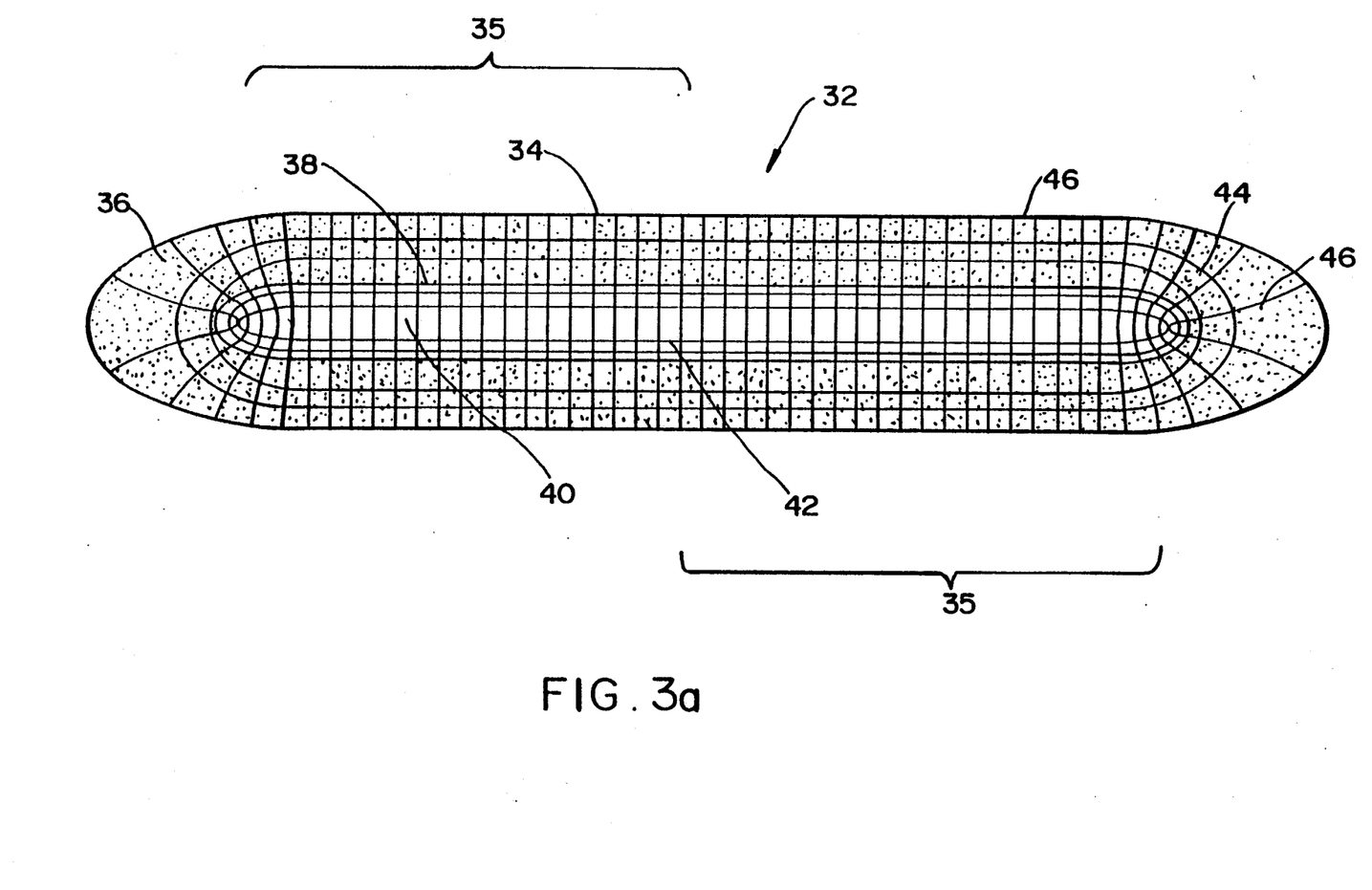
FIG. 3(a) exhibits the preferred embodiment of the present invention.

The capillary 32 portrayed in FIG. 3a is generally oblong in shape. An exterior surface 34 encloses a capillary wall 36 which defines two generally radial channels 35 that extend in opposite directions from the center of the capillary along the transverse axis of the tube. The distance around the wall 36 is the total perimeter of the capillary 32. The width of each radial channel is denoted by reference numeral 37 and is demarcated by the greatest orthogonal distance across the walls 38 of the interior surface of the capillary 32. The mixture of solute and buffer solution is conveyed through central area 40. For a complete description of the operation of the capillary electrophoresis separation instrument, the reader is referred to the parent patent application entitled "Capillary Zone Electrophoresis Cell System" by the same inventor which has been incorporated into this application by reference. Reference numerals 42 and 44 point out isothermal lines while electric field lines are indicated by numeral 46. The present invention has been designed to minimize the distance from any point in the cross-sectional area to the nearest point on the interior wall of the capillary. In the preferred embodiment, the maximum channel width 37 is approximately fifty microns. The ratio of the channel length 35 to channel width 37 is generally equal to two or greater.

Figure 3B:
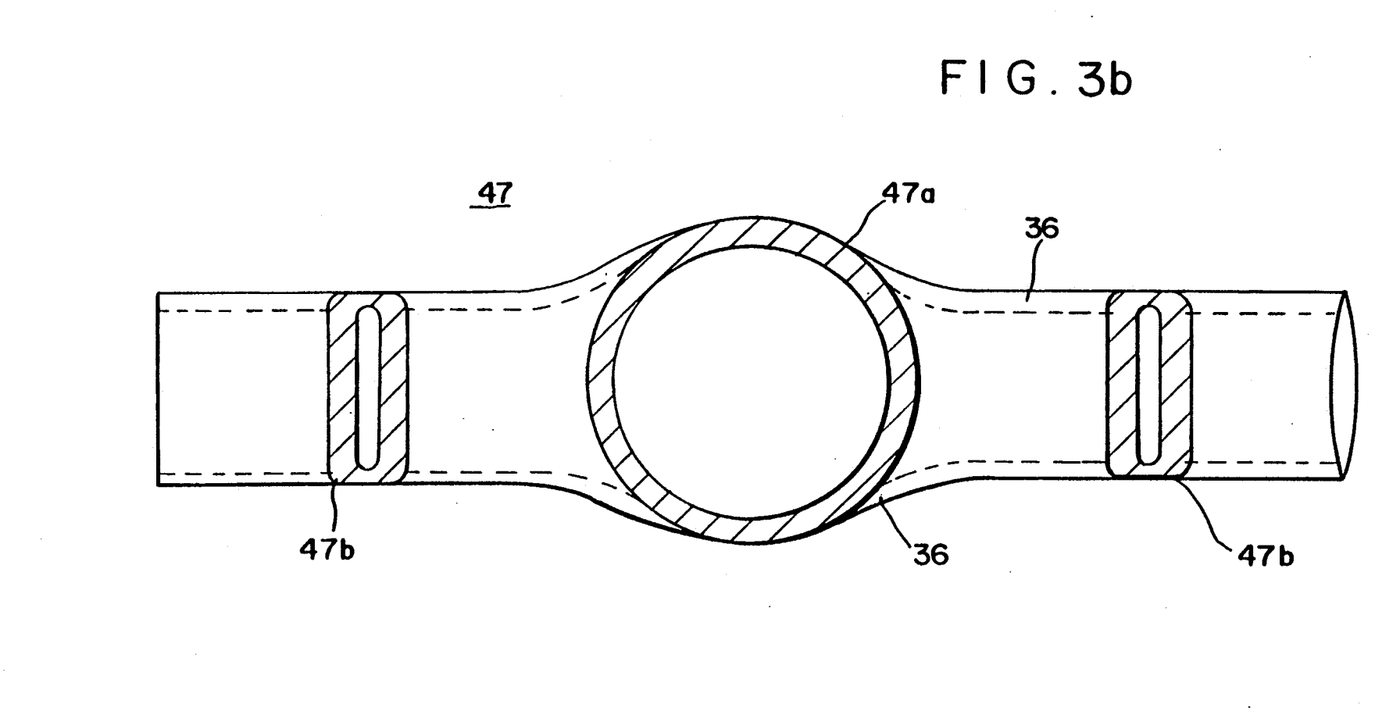
FIG. 3(b) is a rotated section illustration of an alternative embodiment of the invention which also incorporates aspects of the inventor's previous invention, The Capillary Zone Electrophoresis Cell System.

FIG. 3(b) depicts an alternative embodiment 47 of the present invention that utilizes an expanded cell 47a which is integrally formed within the capillary 36. Two cross-sectional portions 47b are shown on each side of the central cell 47a. The reader is encouraged to refer to the inventor's previous patent application, the "Capillary Zone Electrophoresis Cell System," for further details. Both the previous and the present invention are designed to improve detector sensitivity.

Figure 4A:
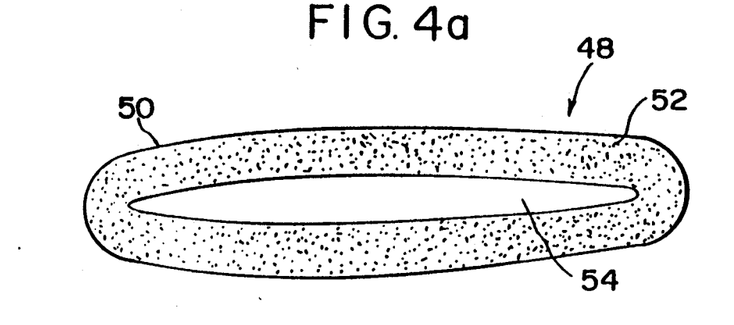
Figure 4B:
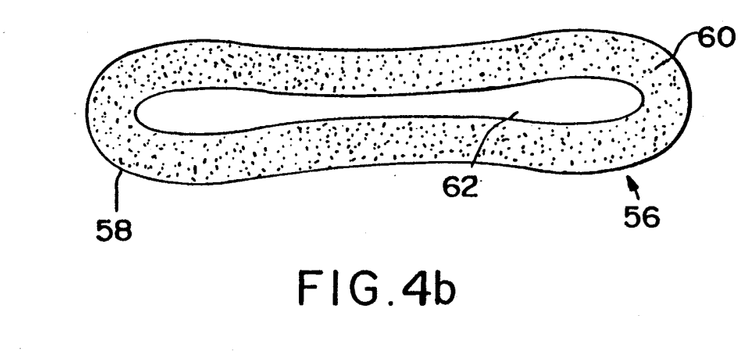
Figure 5:
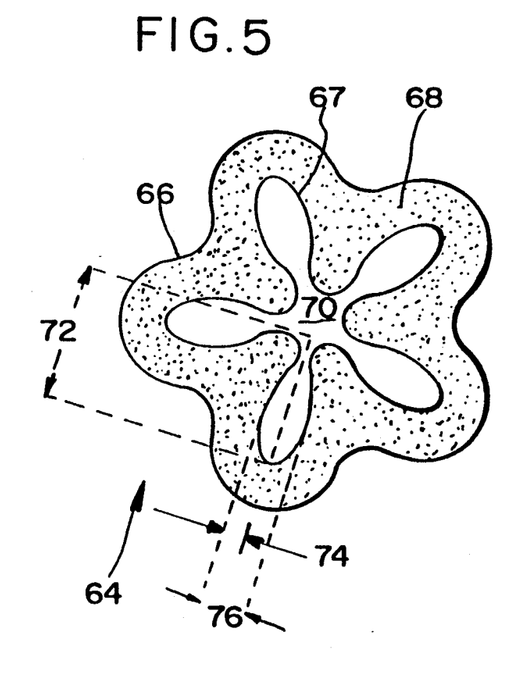
FIG. 5 portrays an "asterisk" pattern.

FIGS. 4(a), 4(b), and 5 illustrate alternative embodiments of the present invention. Capillary 48 includes an exterior 50, a wall 52, a central area 54, and has a generally oval cross-section. Capillary 56 comprises an exterior 58, a wall 60, a central zone 62, and resembles a figure-eight shape. The "asterisk" or star-shaped profile 64 pictured in FIG. 5 provides an alternative approach to maximizing the ratio of total cross-sectional area to total channel length. The asterisk capillary 64 has an exterior 66, radial channels 67, a capillary wall 68, and a central area 70. The length of each radial channel 67 is denoted by dimension 72, while the center-to-wall distance and maximum width of the channels 67 are marked by reference numerals 74 and 76.

Figure 6:
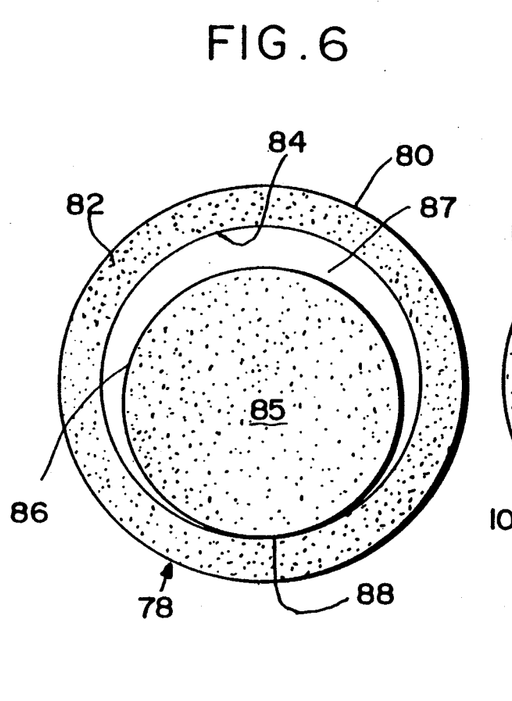
Figure 7:
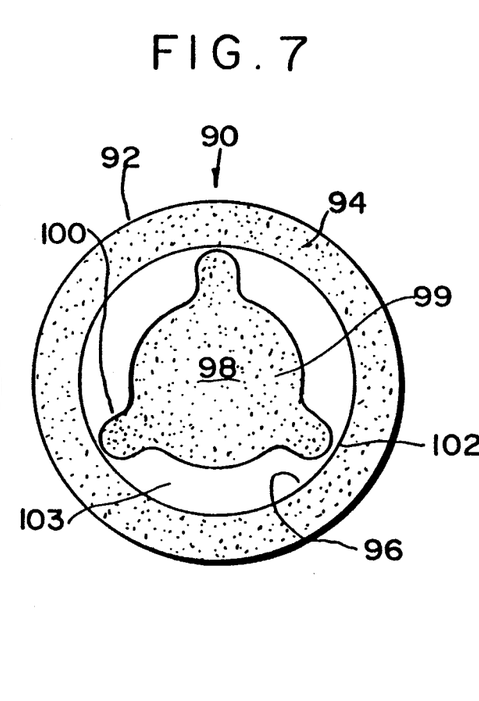

FIGS. 6 and 7 represent yet another class of alternative embodiments of the Electrophoresis Capillary with Dispersion-Inhibiting Cross-Section. FIG. 6 depicts a circular capillary 78 that includes a solid interior filament. A conventional circular capillary 80 having a wall 82 and an inside diameter 84 encloses a filament 85 having an outside diameter 86. Reference numeral 87 denotes the channel in this embodiment. The capillary 80 and the filament 85 touch at contact point 88. The solid interior filaments may extend along the entire length of the separation column and may or may not be bonded to the outside capillary.

Figure 8:
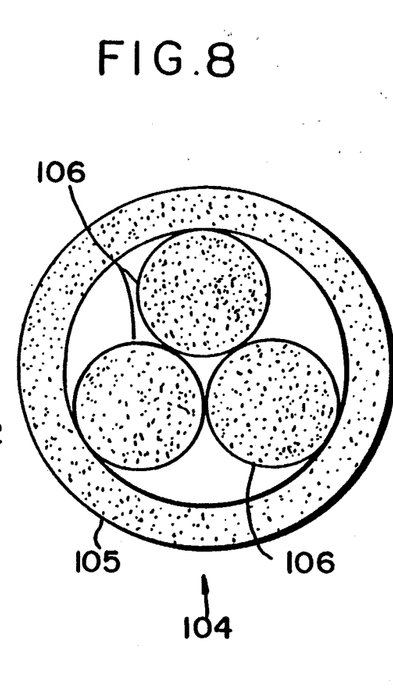
FIG. 8 reveals a capillary which circumscribes three solid filaments.

FIG. 7 reveals yet another variation that maximizes cross-sectional area while holding the thermal gradient distance to a minimum. Another circular capillary 90 having an exterior 92 and a wall 94, and an inner diameter 96 encloses a solid interior filament 98 having an outside diameter 99 and three contact appendages 100. The filament 98 touches the capillary at three points 102. The channels 103 in this version of the invention lie between the capillary interior 96 and the outside diameter 99 of the filament 98. FIG. 8 depicts a circular capillary 104 circumscribing three solid filaments 106.

Figure 9:
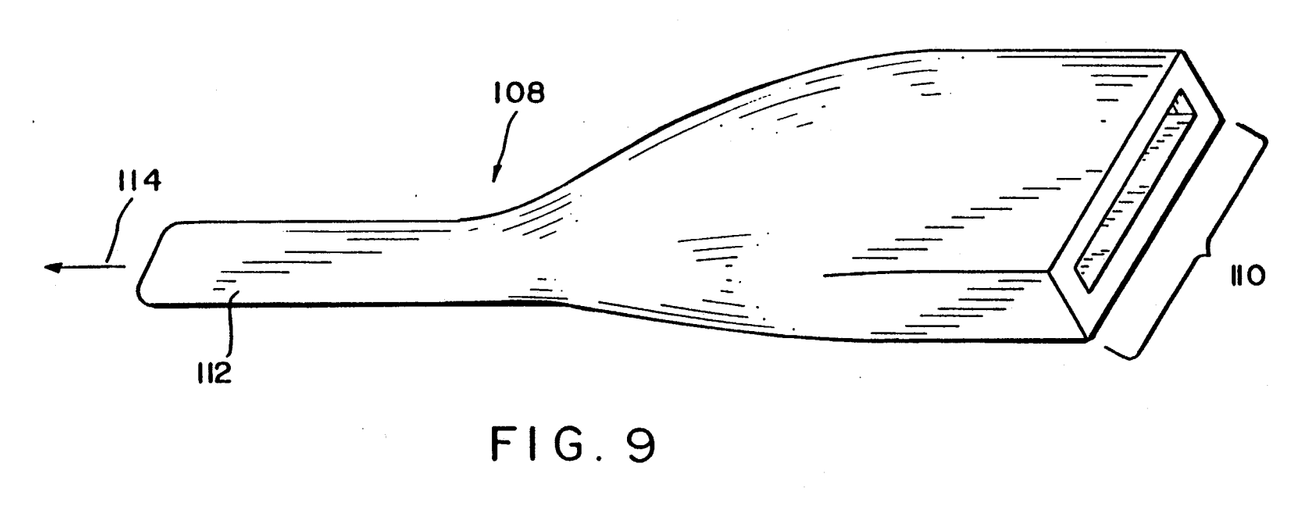
FIG. 9 is a perspective view of a cast pre-form of fused silica which is drawn down to fabricate a flattened capillary having a non-circular cross-section.

The processes utilized to fabricate the present invention are substantially the same as those employed to manufacture conventional round capillaries. A large ingot or pre-form of fused silica is drawn into a desired cross-section. The original ingot is much larger than the final product but has essentially the same cross-section. Local heating sources are used to shape the final product. A typical cast pre-form 108 of fused silica having a rectangular cross-section is exhibited in FIG. 9. The larger cross-section 110 shown at the right side of the drawing is held in place while the opposite end 112 is drawn down into the resulting capillary. The direction of force applied to the pre-form is indicated by arrow 114.

One measure of the performance of separation instruments concerns the concept of "theoretical plates," a statistical term which is used to measure the resolution power of a separation system. A relatively small capillary having a diameter of fifty microns is capable of resolving approximately one million theoretical plates. If large conventional circular capillaries are used, this figure drops rapidly by several orders of magnitude, indicating that the separation capacity of the column has been seriously degraded. By substantially eliminating eddy currents, viscosity gradients, and gravity siphoning, the Electrophoresis Capillary with Dispersion-Inhibiting Cross-Section can maintain unprecedented resolution levels of one million theoretical plates and above. The present invention combines the selectivity of a conventional, smaller, round capillary with the sensitivity of a capillary which is ten times larger.

Figure 10:
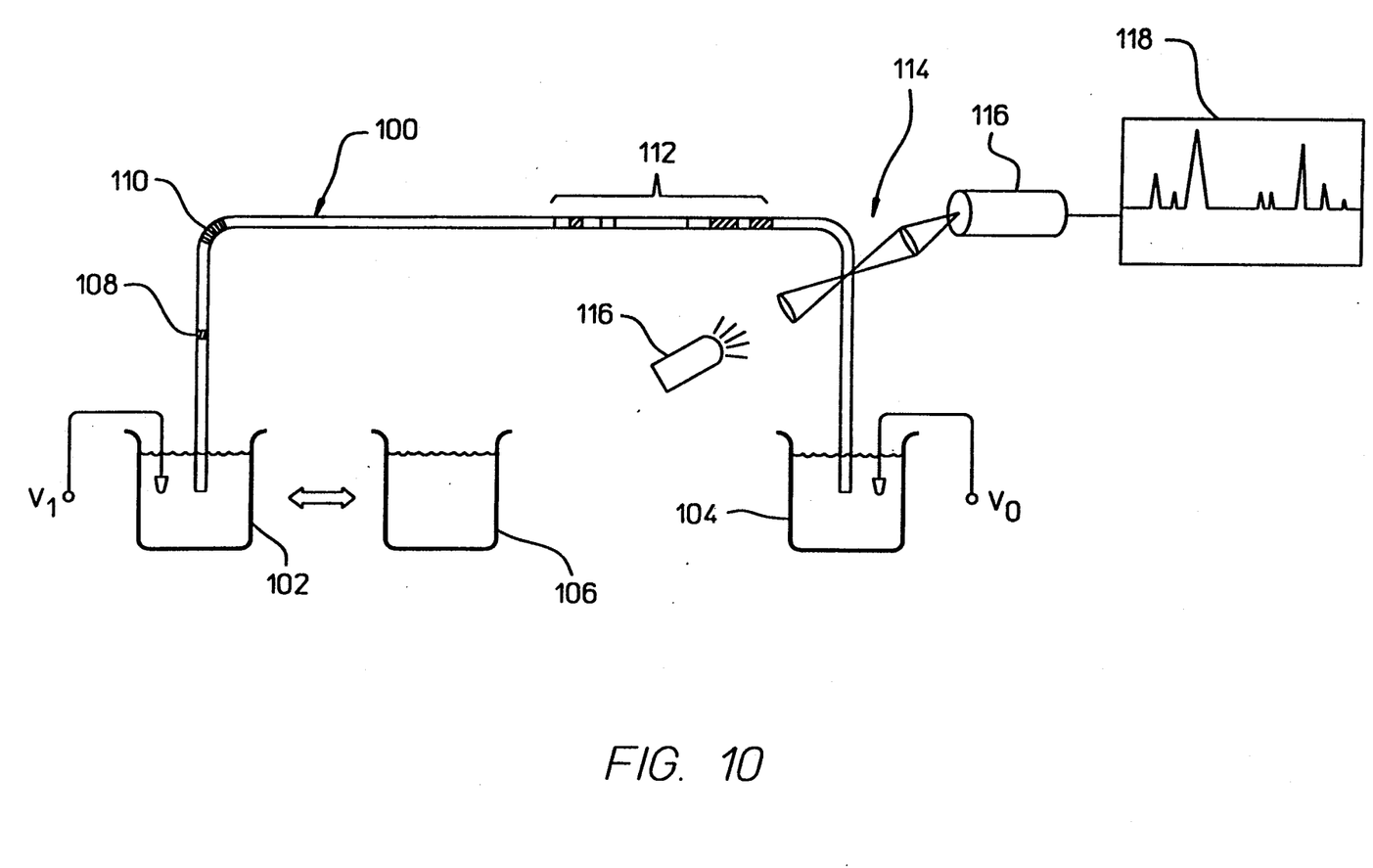
FIG. 10 illustrates schematically a capillary zone electrophoresis apparatus that can advantageously incorporate the various embodiments of the invention.

FIG. 10 illustrates schematically a capillary zone electrophoresis (CZE) apparatus that can advantageously incorporate the various embodiments of the invention. The general structure of a CZE apparatus is well known and is not part of this invention.

In a CZE system, a separation capillary 100 extends (either as a single capillary or as a connected sequence of capillaries or other tubing) from a buffer reservoir or vial 102 to a waste reservoir or vial 104. The capillary may be in the form of any of the embodiments of the invention described above. The buffer vial 102 holds a conventional buffer, which is held at a first electrical potential $V_1$. After allowing a certain amount of the buffer to enter the capillary 100, the buffer vial is normally exchanged with a sample vial 106, which holds a sample of the analyte. After a small amount of the analyte enters the capillary (indicated as a compact band 108), the end of the capillary is once again put into contact with the buffer.

As the analyte migrates through the capillary, it enters a main separation region (whose approximate beginning is indicated as 110 in FIG. 10), where the analyte begins to separate into more clearly distinguishable separation bands (illustrated generally in the region labelled 112). The separation bands then pass a detection region 114, where conventional detection circuitry is used to sense the passage (and sometimes even the spectral properties of) the various bands. In one known type of system, light from a UV source 116 is directed through the capillary 100 in the detection region 114 and is sensed by a conventional detector 116. Separation peaks are then displayed on a conventional display device 118 (such as a strip-chart recorder).

In order to speed up separation by inducing electroosmotic flow, the upstream end of the capillary is held at a different electrical potential, $V_1$, than the downstream end, which is held at $V_0$. $V_0$ is typically several kilovolts lower than $V_1$, although other configurations, with multiple potentials and various electrode arrangements are also commonly used.

Although the present invention has been described in detail with reference to a particular preferred embodiment, persons possessing ordinary skill in the art to which this invention pertains will appreciate that various modifications and enhancements may be made without departing from the spirit and scope of the claims that follow.

What is claimed is:

1. A capillary electrophoresis apparatus for separating and detecting constituent components of an analyte, comprising:
   a buffer reservoir;
   a waste reservoir;
   a separation capillary;
   high-voltage means for applying an electric field over the length of the separation capillary;
   detection means for detecting separation bands of the analyte corresponding to those constituent components of the analyte that have moved differentially within the separation capillary;
   in which the separation capillary is made of a drawn material and has:
   a narrow-bore main separation region that is connected to the buffer reservoir and has an inner wall enclosing a buffer fluid and the analyte;
   a detection region connected to the main separation region and to the waste reservoir and located adjacent to the detection means;
   wherein
   the main separation region has a non-circular cross-section with an internal channel length and an internal channel width;
   the internal channel length is at least twice the internal channel width;
   the detection region of the separation capillary is formed as an expanded cell, with a larger cross-sectional area than that of the cross-section of the main separation region, whereby the detection path length and thus the detection sensitivity of the apparatus are increased;
   whereby a rise in temperature in a central portion of the cross-section caused by Ohmic heating of the buffer fluid is minimized, thereby reducing band-broadening of separation peaks corresponding to the separated constituents of the analyte, which is introduced into the main separation region.

* * * * *